(12) United States Patent
Kuenen et al.

(10) Patent No.: US 11,350,859 B2
(45) Date of Patent: Jun. 7, 2022

(54) PATIENT MONITORING

(71) Applicant: KONINKLIJKE PHILIPS N.V., Eindhoven (NL)

(72) Inventors: Maarten Petrus Joseph Kuenen, Veldhoven (NL); Rick Bezemer, Amsterdam (NL); Laurentia Johanna Huijbregts, Eindhoven (NL); Joachim Kahlert, Aachen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 540 days.

(21) Appl. No.: 16/470,636

(22) PCT Filed: Dec. 20, 2017

(86) PCT No.: PCT/EP2017/083694
§ 371 (c)(1),
(2) Date: Jun. 18, 2019

(87) PCT Pub. No.: WO2018/115049
PCT Pub. Date: Jun. 28, 2018

(65) Prior Publication Data
US 2020/0085357 A1    Mar. 19, 2020

(30) Foreign Application Priority Data
Dec. 20, 2016   (EP) .................... 16205203

(51) Int. Cl.
*A61B 5/1455*   (2006.01)
*A61M 16/00*   (2006.01)
*A61B 5/00*    (2006.01)

(52) U.S. Cl.
CPC .......... *A61B 5/14551* (2013.01); *A61B 5/682* (2013.01); *A61M 16/022* (2017.08); *A61M 2230/205* (2013.01)

(58) Field of Classification Search
CPC . A61B 5/1455; A61B 5/0205; A61B 5/14551; A61B 5/14552; A61B 5/6813; A61B 5/682; A61B 5/14532
See application file for complete search history.

(56) References Cited

U.S. PATENT DOCUMENTS 6,898,452 B2 *  5/2005  Al-Ali ............... A61B 5/14551
                                                600/323
7,263,395 B2    8/2007  Chan et al.
(Continued)

FOREIGN PATENT DOCUMENTS

WO    2018115082 A1    6/2018

OTHER PUBLICATIONS

Nitzan, M. et al., "The measurement of oxygen saturation in arterial and venous blood", IEEE Instrumentation and Measurement Magazine, Jul. 2008.

(Continued)

*Primary Examiner* — Chu Chuan Liu

(57) ABSTRACT

Presented are concepts for monitoring cardio-respiratory function of a patient. One such concept employs an optical sensor unit (10) for sensing light from tissue of the patient in response to temporary airway pressure changes provided via a respiratory support unit (50). By sensing variations in blood volume in the central site vein in response to temporary airway pressure changes, venous information of the person may be obtained.

13 Claims, 4 Drawing Sheets

(56) References Cited

U.S. PATENT DOCUMENTS

| | | | |
|---|---|---|---|
| 2007/0000494 A1* | 1/2007 | Banner | A61B 5/0205 |
| | | | 128/204.23 |
| 2010/0057045 A1 | 3/2010 | Albritton | |
| 2010/0057046 A1 | 3/2010 | Stevens et al. | |
| 2010/0152599 A1 | 6/2010 | Duhamel | |
| 2013/0066175 A1 | 3/2013 | Addison et al. | |
| 2016/0019283 A1* | 1/2016 | Gibson | G16H 10/60 |
| | | | 706/14 |

OTHER PUBLICATIONS

Phillips, J. et al., "Modulation of finger photoplethysmographic traces during forced respiration: Venous blood in motion?", IEEE Engineering in Medicine and Biology Society, Conference, Aug. 2012.

Shafqat, K. et al., "Instantaneous venous oxygenation estimation using the Photoplethysmograph (PPG) waveform", Journal of Physics: Conference Series 307, 2011.

* cited by examiner

PATIENT MONITORING

CROSS-REFERENCE TO PRIOR APPLICATIONS

This application is the U.S. National Phase application under 35 U.S.C. § 371 of International Application Serial No. PCT/EP2017/083694, filed on 20 Dec. 2017, which claims the benefit of European Application No. 16205203.9, filed on 20 Dec. 2016. These applications are hereby incorporated by reference herein.

FIELD OF THE INVENTION

This invention relates to patient monitoring, and more particular to monitoring cardio-respiratory function of a patient.

BACKGROUND OF THE INVENTION

Monitoring of a patient, and in particular monitoring of cardio-respiratory function of a patient, is often relevant for an enhanced diagnostics and therapy planning for the patient. Examples of patients for which monitoring of cardio-respiratory function may be beneficial include those suffering from medical conditions such as chronic obstructive pulmonary disease (COPD), sleep-related problems (sleep disordered breathing (SDB) or insomnia, for example), respiratory disorders, asthma, and the like.

For example, the oxygenation level of blood (SO2) is an important value that may be indicative of human health status because it indicates the availability of oxygen to all tissues. Usually, SO2 refers to the oxygen saturation percentage in arterial blood (SaO2), after gas exchange in the lungs where carbon dioxide is released and oxygen is taken up.

Blood oxygenation can be measured by optical techniques, such as photoplethysmography (PPG), because oxygenated and deoxygenated haemoglobin have a different colour. This can be exploited by transmitting light two different optical wavelengths (typically at red and infrared colours) through tissue (usually the finger tip) and then measuring the light intensity with a photodiode. Such a method for measuring arterial oxygenation with PPG is called "pulse oximetry", and the arterial oxygenation measured in this way is referred to as "SpO2".

In pulse oximetry, it is assumed that attenuation in tissues, bone structures, and venous blood remains constant over time scales of a few heart beats or less, and that the observed dynamic variations in light intensity are only due to the arterial blood volume that varies with each heartbeat. These changes in light intensity (corresponding to the heart beats) give rise to an AC component of the PPG signal, while the much slower fluctuating component is a DC component of the PPG signal. To derive the SpO2 value, the relative changes in detected light (e.g. changes that are assumed to be caused by arterial blood because they pulsate due to the heart beat, as compared to the slower fluctuating component) at one wavelength ($\lambda 1$) are compared to those at another wavelength ($\lambda 2$), with other absorption characteristics for oxygenated and deoxygenated haemoglobin, resulting in the following ratio of ratios (RR): $RR=(AC/DC)_{\lambda 1}/(AC/DC)_{\lambda 2}$.

This ratio is subsequently used in a formula to derive the arterial oxygenation. Often, a linear relationship is assumed: $SpO2 = a \cdot RR + b$, wherein a and b are calibration constants.

The oxygenation level in the venous system (SvO2) is often overlooked. However, whereas SaO2 describes the availability of oxygen to tissues, SvO2 allows the derivation of how much oxygen is actually taken up in the organs and tissues. SvO2 is, therefore, a clinically relevant parameter in several settings (e.g. in patient monitoring during surgery procedures). Together, SaO2 and SvO2 provide highly relevant clinical information in a wide range of settings.

Similarly to SaO2, SvO2 can be measured by inducing a venous blood volume change and subsequently measuring the oxygen saturation from optical signals at two different wavelengths. In comparison to SaO2, however, the measurement of SvO2 is more complicated, mainly for the following two reasons: (i) SaO2 is much more easily defined than SvO2, since all blood in the arteries of the systemic circulation essentially have the same oxygenation level, as the blood is distributed through all systemic arteries before any gas exchange takes place. On the contrary, venous blood is first collected from the microcirculation and eventually pooled together in the right atrium. This severely constrains the choice of measurement sites for obtaining the central venous oxygenation, and has resulted SvO2 measurement concepts that are intrusive in nature; and (ii) There is no natural mechanism (or 'venous' equivalent of the beating heart) showing up as clearly in the signal as the pulse does for arterial blood to distinguish venous blood from arterial blood, bones, and tissues. This makes it difficult to infer SvO2 based on measured light absorption spectra.

Thus, there exists a need for non-invasive or unobtrusive monitoring concepts for monitoring cardio-respiratory function of a patient. Further, it would be particularly advantageous for concepts to be suitable for obtaining venous information (such as venous oxygen saturation, SvO2). Such non-invasive and/or unobtrusive monitoring concepts may be beneficial for enhanced diagnostics and therapy planning in relation to many medical conditions.

SUMMARY OF THE INVENTION

The invention aims to at least partly fulfil one of the aforementioned needs. To this end, the invention provides devices, methods, computer program products and systems as defined in the independent claims. The dependent claims provide advantageous embodiments.

Thus, the invention provides an apparatus and a corresponding method for monitoring cardio-respiratory function of a patient. Embodiments of the apparatus may comprise: an optical sensor unit adapted to detect light from tissue of the patient and to generate sensor output signals based on the detected light; a respiratory support unit adapted to provide a controllable positive airway pressure to an airway of the patient; a control unit adapted to control the respiratory support unit to a provide a first positive airway pressure to the airway of the patient and to receive a first sensor output signal from the optical sensor unit, the first sensor output signal being based on light detected from the tissue in response to provision of the first positive airway pressure, and further adapted to control the respiratory support unit to provide a second, different positive airway pressure to the airway of the patient and to receive a second output signal from the optical sensor unit, the second sensor output signal being based on light detected from the tissue in response to provision of the second positive airway pressure; and a processing unit adapted to determine venous information of the patient based on the first and second sensor output signals.

US2010/057046 discloses a system for therapy adjustments based on sensed information. An example is closed-loop ventilation, wherein the ventilation therapy is adjusted based on physiological parameters of the subject that are measured. One such a parameter is venous oxygenation, which is measured invasively with a probe inside a patient's vein. US2010/0152599 describes an oral appliance compliance monitoring system and method. The oral appliance is suitable for wearing in a patient's oral cavity during sleeping periods and has one or more sensors measuring a variety of conditions such as oxygen saturation levels in the oral cavity mucosa.

Proposed embodiments are based on using a respiration support device (such as a CPAP device) which provides a controllable positive airway pressure during natural respiration of a patient, thus potentially providing measurement of respiration cycle, air flow and pressure. Light from tissue of the patient may be detected by an optical sensor unit (such as a photoplethysmography (PPG) sensor for example) while the respiration support device provides a baseline airway pressure (e.g. a continuous, low pressure level) to the airway of the patient. The respiration support device may then be controlled to provide a temporary change (e.g. increase) in the airway pressure (which may be triggered the patient's heart rate and/or respiration rate), and a second measurement of the light from tissue of the patient may then be detected (e.g. as a specific time period after the temporary pressure change). Venous information (such as venous oxygen saturation, SvO2, for example) of the patient may then be determined based on the two light measurements.

It may therefore be proposed to induce temporary changes in positive airway pressure (e.g. provide pressure stimuli) and monitor variations in blood volume in response to the temporary changes/stimuli so as to obtain venous information of the patient. Rather than a mechanical ventilator, a pressure support device may be used to modify airway pressure of the patent, and control of the changes in pressure may be based on (e.g. gated by) the heart rate and/or the respiration rate of the patient.

By way of example, the respiratory support unit may be implemented by a CPAP device, in which the pressure may be controlled by the spontaneous breathing pattern (monitored by the PAP device) or in triggered fashion (based on the signals from the optical sensor unit).

Instead of a baseline pressure increase, other pressure challenges could be adopted. Examples may include a pressure decrease from a high baseline pressure, or pressures modulated by the respiration cycle as is common in BiPAP systems. A further example could be a 'cough assist' device which creates a strong positive and negative pressure amplitude to amplify the blood pooling in extrathoracic veins. An alternative method to apply a pressure stimulus signal might be to induce a specific pressure frequency, e.g. by using the forced oscillation technique (FOT). An advantage of using a FOT is that the technique is readily available. However, induced venous changes might be better visible when using lower frequencies than used in classical FOT.

Accordingly, there may be provided a tool for determining and/or monitoring a venous information that can be used by a medical professional, a general practitioner without the support of a trained cardiologist, for example. It may assist in the diagnosis of dynamic changes of the preload and blood accumulation in heart failure patients. Similarly, it may help to diagnose and stratify persons who are at the onset of developing heart failure and pulmonary edema. Embodiments may also be used to verify the success of a cardiac therapy and/or to monitor disease progression or exacerbation.

Also, embodiments may be used for detecting or monitoring sleep apnea in a sleep study. For example, proposed embodiments may be employed to detect obstructive and central apnea and may distinguish between these. Further, an embodiment may be used to monitor the cardio-respiratory response of a ventilation therapy and to better control the device settings of a pressure support therapy in COPD and OSA patients.

By way of example, embodiments may be used by a general physician or (medically) un-trained person without the support of a trained cardiologist. This may alleviate a need for close monitoring by medical professionals. It may also reduce a need for medical intervention or treatment. Embodiments may therefore relieve healthcare requirements/resources.

The optical sensor unit may be adapted to be positioned at vasculature draining into the internal jugular vein of the patient. For example, the optical sensor unit may comprise a sublingual optical sensor unit adapted to be positioned at sublingual vasculature of the patient's tongue, to detect light from the sublingual vasculature and to generate the sensor output signals based on the detected light. Thus, some embodiments may be based on using the sublingual vein or vasculature of a patient's tongue to look at the venous pulse and variations in blood volume in the sublingual vein or vasculature so as to obtain information on cardio-respiratory interactions. The advantage of the sublingual vein is that it lies close to the surface and that the sublingual skin is very thin and optically transparent. Also, the bottom side of the tongue is a highly perfused area. Those properties make the bottom side of the tongue well-suited for optical monitoring for example. Further, compared to many other veins or vasculature in other places in the body, the sublingual vein or vasculature is of special interest because it drains into the internal jugular vein, which then drains into the vena cava; there is therefore a close connection to the central veins and the right side of the heart. Especially in lying position information for the right side of the heart and the central veins can be seen derived from the sublingual vein.

It may therefore be proposed to arrange or adapt an optical sensor unit to be aimed at the sublingual vasculature/area on the bottom side of a patient's tongue. This may, for example, enable more of the venous component to be seen in the sensor signals. Proposed embodiments may therefore leverage the raw signal of the optical sensor.

In other embodiments, other sites with veins draining into the internal jugular vein are probed. Examples are the nose, the eye, the inner ear and the forehead.

Signals from the optical sensor unit that are representative of detected light from the tissue may be used to provide information on cardio-respiratory parameters like respiration rate (RR), respiration rate variability (RRV), onset of inspiration, onset of expiration, duty cycle of respiration, Cheyne-Stokes respiration, obstructive sleep apnea (OSA), central sleep apnea (CSA), distinction between OSA and CSA, obstructive flow limitation (Hypopnea), mean transmural pressure, mean blood accumulation, the presence of edema, sighing, yawning, coughing, paced breathing, and pursed breathing.

It should be noted that probing only the sublingual vein might not be possible (because the positioning comes very critical) and it might not be desirable either. When an area is probed that is only a very short distance from the vein, the venules still give the desired signal representative for the respiratory- and blood accumulation-related information and next to that, information is obtained from the arterioles in that area, from which the heart rate, heart rate variability and arterial blood oxygenation can be obtained. For those reasons, in this patent, when we refer to 'at the sublingual vein' or 'sublingual vasculature', we mean not only aimed solely at the sublingual vein, but also at an area at a very close distance from (i.e. proximate to) the sublingual vein, where still the information from the venules that drain in the sublingual vein can be derived from the signal. This is preferably at a distance smaller than 1 cm from the sublingual vein, and more preferably at a distance smaller than 5 mm from the sublingual vein. In this way, it will be understood that, in proposed embodiments, a sublingual optical sensor unit may be adapted to be positioned at vasculature draining into the internal jugular vein of the patient, such as sublingual vasculature or sublingual venous vasculature of the patient's tongue.

The control unit may be adapted to control the respiratory support unit to provide a pulsed application of the second, different positive airway pressure to the airway of the patient. Further, the control unit may be adapted to control the respiratory support unit to provide the second, different positive airway pressure to the airway of the patient based on at least one of: the heart rate; and the respiration rate of the patient. Thus, triggering may be done based on the heart rate and or respiration rate of the subject, and these could be measured from the optical sensor output signal signals. By way of further example, the timing of the first and second sensors output signals may be based on the phase in at least one of: the cardiac cycle; and the respiratory cycle.

The respiration rate may also be measured based on the pressure and/or airflow measurement that is integrated in the respiratory support unit. Thus, in some embodiments, the processing unit may be adapted to determine at least one of: the heart rate; and the respiration rate of the patient based on at least one of: a sensor output signal from the optical sensor; and positive airway pressure provided by the respiratory support unit to the airway of the patient. In addition, other sensors may be used to measure heart rate and/or respiration rate and trigger the air pressure change, e.g. ECG or accelerometer.

In some embodiments, the control unit may be adapted to control the respiratory support unit based on the determined venous information.

The optical sensor unit may be used either in a reflective mode or a transmissive mode. In an exemplary embodiment, the optical sensor unit may comprise at least one of: a PPG sensor; a laser speckle sensor; a laser Doppler sensor; and a camera. It is noted that PPG sensors exist which, when placed on the finger or ear lobe, may enable the derivation of RR from the sensor signal. However, for sensors placed at these locations, it is practically impossible to see the RR by eye from the raw PPG signal. Therefore, RR can only be derived with relatively complex algorithms, which generally take into account modulations in frequency, amplitude and DC-level. Even then, the derived RR is not always correct. In contrast, the raw PPG signal of a PPG sensor at a site with vasculature draining into the internal jugular vein (such as nose, inner ear, eye, forehead, and especially the tongue) clearly shows RR, onset of inspiration, onset of expiration and depth of inspiration thereby potentially avoiding the need for complex algorithms and/or extensive processing resources.

Embodiments may further comprise a light source adapted to illuminate the body tissue of the patient. The light source may be adapted to emit first light having a wavelength within a first range of wavelengths and to emit second light having a wavelength within a second, different range of wavelengths, or more than one light sources might be used, which each have their own specific wavelength band. By way of example, the first range of wavelength may comprise visible light and the second range of wavelengths may comprise infra-red light. In order to derive SO2, red and infra-red light are commonly used. Since blood in the veins and venules contains more deoxygenated blood than blood in the arteries and arterioles and since red light is absorbed substantially more be deoxygenated blood than by oxygenated blood (while the absorption in infra-red is similar), red light is especially suitable to derive venous information. In order to have a further distinction between venous and arterial information, the red signal and the infra-red signal could be compared, e.g. the infra-red signal might (preferably after weighing) be subtracted from the red signal.

Embodiments may further comprise an output interface adapted to generate an output signal representative of determined or calculated venous information. For example, a user may be advised of a SO2 value below a predetermined acceptable threshold.

Embodiments may further comprise a user input interface adapted to receive a user input signal representative of at least one of: environmental information; patient information; and a limit value representative of an acceptable limit of a cardio-respiratory value. Embodiments may therefore be thought of as providing an interface which enables a user to further specify information or data that may be relevant for the purpose of determining or monitoring a cardio-respiratory value. Such user-specified information may enable unique traits, circumstances and/or conditions specific to the user or the environment to be accounted for when determining or monitoring a cardio-respiratory value.

Thus, there may be provided a tool which enables a user to further specify factors to be included in the determination or monitoring of cardio-respiratory function, e.g. by specifying a value or value range for a user attribute or activity. Embodiments may therefore provide input options, increasing the flexibility and power of risk of cardio-respiratory monitoring.

In some embodiments, the apparatus may further comprise a communication interface adapted to communicate with one or more databases so as to obtain at least one of the information that may be used in determining or monitoring a venous information.

There may be provided a portable computing device comprising apparatus for monitoring a cardio-respiratory function of a patient according to a proposed embodiment.

The system may further comprise a device for providing a graphical or non-graphical (e.g. auditory) user interface, wherein the user interface is adapted to communicate information about detected or monitored venous information or cardio-respiratory function of a patient to a user.

Embodiments may comprise a client device comprising a data processor device. This may be a standalone device adapted to receive information from one or more remotely positioned information sources (via a communication link for example) and/or even adapted to access information stored in a database for example. In other words, a user (such as a medical professional, technician, researcher, patient etc.) may have an appropriately arranged client device (such as a laptop, tablet computer, mobile phone, PDA, etc.) which provides a system according to an embodiment and thus enables the user to provide data or information for the purpose of monitoring cardio-respiratory function of a patient.

The system may comprise: a server device comprising the at least one processor, where the server device may be configured to transmit generated instructions for determining and/or displaying a cardio-respiratory function of a patient to a client device or communication network. In such a configuration, display instructions are made available by a server. A user may therefore link with the server to work with the system.

The processor may be remotely located from the display device, and a control signal may thus be communicated to the display device via a communication link. Such a communication link can be e.g. the internet and/or a wireless communication link. Other suitable short-range or long-range communication links and/or protocols may be employed. In this way, a user (such as a medical researcher, general practitioner, data analyst, engineer, patient etc.) may have an appropriately arranged device that can receive and process information according to an embodiment for monitoring a cardio-respiratory function of a patient. Embodiments may therefore enable a user to remotely monitor cardio-respiratory function of a patient using a portable computing device, such as a laptop, tablet computer, mobile phone, PDA, etc. Embodiments may also enable data retrieval after a monitored time period.

The system may further comprise: a server device comprising the at least one processor; and a client device comprising a display device. Dedicated data processing means may therefore be employed for the purpose of monitoring a cardio-respiratory function or venous information of a patient, thus reducing processing requirements or capabilities of other components or devices of the system.

Thus, it will be understood that processing capabilities may therefore be distributed throughout the system in different ways according to predetermined constraints and/or availability of processing resources.

According to another aspect of the invention, there may be provided a respiratory device comprising apparatus for monitoring cardio-respiratory function of a patient according to any preceding claim. For example, embodiments may propose the use of an optical sensor unit placed in an oral appliance, wherein the oral appliance on the lower teeth houses the sensor. In this way, the optical sensor unit may be stably positioned in the mouth, thereby reducing motion artefacts. The oral appliance may, for example, be designed such that the tongue can rest directly on the optical sensor. In some embodiments, the optical sensor may be adapted to be movable with respect to the oral appliance (e.g. under the control of a mechanical or electro-mechanical arrangement), thereby enabling the positioning of the optical sensor to be optimised or personalised to a specific-patient for example.

According to yet another aspect of the invention, there may be provided a method for monitoring cardio-respiratory function of a patient, the method comprising: controlling a respiratory support unit to a provide a first positive airway pressure to an airway of the patient; obtaining, from an optical sensor unit, a first sensor output signal based on light detected from the tissue in response to provision of the first positive airway pressure; controlling the respiratory support unit to provide a second, different positive airway pressure to the airway of the patient; obtaining, from the optical sensor unit. a second sensor output signal based on light detected from the tissue in response to provision of the second positive airway pressure; and determining venous information of the patient based on the first and second sensor output signals.

The step of controlling the respiratory support unit to provide the second, different positive airway pressure to the airway of the patient may be based on at least one of: the heart rate; and the respiration rate of the patient, and preferably further comprising providing a control signal to the respiratory support unit by the control unit that is gated by the phase in at least one of: the cardiac cycle; and the phase in the respiratory cycle.

Embodiments may provide concepts for monitoring one or more cardio-respiratory functions of a patient. The proposed concepts may comprise positioning an optical sensor at (e.g. adjacent, proximate, next to, neighbouring, etc.) sublingual vasculature of the patient's tongue. Light transmitted through the sublingual vasculature may be detected by the optical sensor and the detected light may be used (e.g. processed according to one or more algorithms) to determine a value of a cardio-respiratory functions of the patient.

Determining venous information may comprise taking account of historical information relating to previously determined values of venous information for the patient. Further, additional sensors may be employed to detect one or more supplementary values of other physical attributes or parameters of the patient. Such supplementary values may be used in combination with the detected light and/or determined venous information to infer or determine other information (such as an indication of accuracy or reliability, an activity of the patient, or an indication of event occurrence for example) and/or confirm/validate the determined venous information. For this purpose, proposed concepts may employ (or be employed on) at least one processor.

Proposed embodiments may further comprise generating instructions for displaying a GUI on a display device using a processor device, wherein the graphical user interface is adapted to communicate information about detected light from the sublingual vein and/or a determined venous information of the patient to a user. Generating instructions for display of a GUI can mean generating a control signal for use by a display device. Such instructions can be in the form of simple images such as bitmap JPEG or other format. However, such instructions can also be more complex allowing real time build-up of the GUI or parts of the GUI on a regular display device such as for example CRT, LCD, OLED, E-ink or the like.

According to another aspect, there may be provided a computer program product downloadable from a communications network and/or stored on a computer readable medium and/or microprocessor-executable medium wherein the computer program product comprises computer program code instructions, which when executed by at least one processor, implement a method according to a proposed embodiment.

The independent claims define analogous advantages features for method and system claims. The advantages explained for the method herein above and herein below may therefore also apply to the corresponding systems.

BRIEF DESCRIPTION OF THE DRAWINGS

The invention will now be described in detail with reference to the following schematic drawings.

DETAILED DESCRIPTION OF THE EMBODIMENTS

Figure 1:
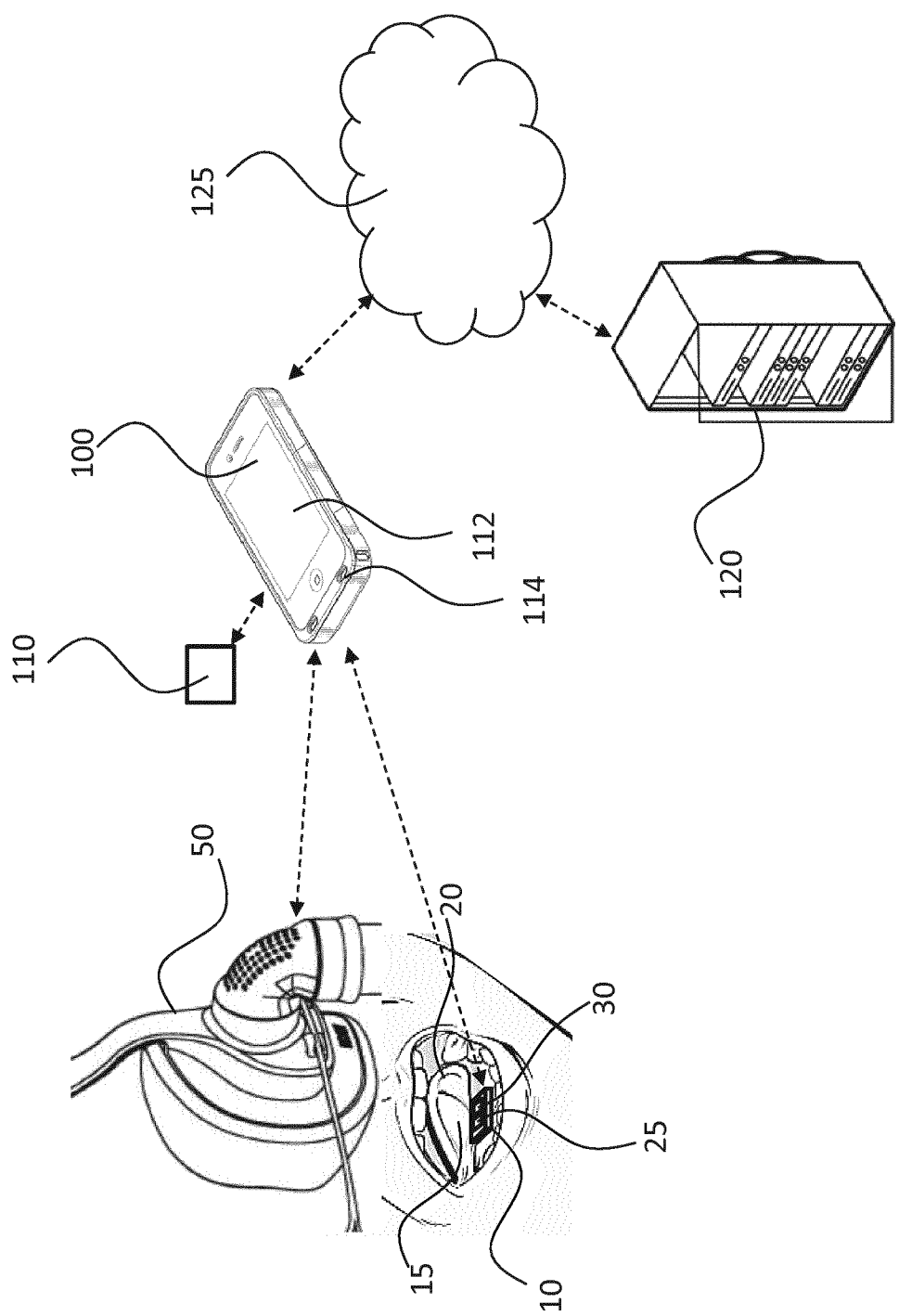
FIG. 1 illustrates an apparatus for monitoring cardio-respiratory function of a patient according to an embodiment.

Proposed embodiments relate to approaches and tools for monitoring cardio-respiratory function of a patient, and in particular to determining venous information of a patient such as SvO2. An optical sensor unit may be employed (e.g. positioned) at vasculature of the patient body tissue so as to detect light from the vasculature. Sensor output signals may then be generated based on the detected light. The signals may be used (e.g. processed or analysed) to determine how the detected light varies in response to a temporary change in positive airway pressure supplied to the patient's airway by a respiratory support unit (such as a CPAP device for example). Based on how the signals vary from before and after the pressure challenge, venous information (such as a value of SvO2) may be calculated.

Embodiments are therefore based on using an optical sensor unit positioned at, against or on vasculature of a patient to detect variations in blood volume which occur in response to airway pressure changes provided by a respiration support device. It may also be proposed to leverage the fact that the sublingual vasculature lies close to the sublingual (i.e. bottom or underside) surface of the tongue and that the sublingual skin is thin and optically transparent. Also, the sublingual vein is directly connected to the jugular vein, thus enabling measurement of SvO2 from a central site. Such properties make the sublingual side of the tongue highly-suited for detecting and monitoring blood-volume variations resulting from respiratory stimuli (such as temporary or spontaneous airway pressure variations caused by a respiration support device in accordance with proposed embodiments).

By way of example, signals from a sublingual optical sensor may be used to provide information on cardio-respiratory parameters including: RR, RRV, onset of inspiration, onset of expiration, duty cycle of respiration, Cheyne-Stokes respiration, OSA, CSA, distinction between OSA and CSA, Hypopnea, mean transmural pressure, mean blood accumulation, the presence of edema, sighing, yawning, coughing, paced breathing, and pursed breathing, for example.

Also, the proposed invention may provide concepts for monitoring one or more cardio-respiratory parameters that can be employed by a general physician or (medically) un-trained person without the support of a trained cardiologist. This may alleviate a need for medical professionals and/or medical intervention, thus potentially relieving healthcare requirements/resources.

Some embodiments may employ a supplementary sensor module, and this may also be adapted to be positioned in the patient's mouth. For example, the supplementary sensor module may comprise a sensor arrangement adapted to sense: movement; pressure; temperature; and/or sound and to generate a supplementary sensor output signal based on the sensed value(s). For example, information regarding sensed motion may be useful for indicating signal quality and/or reliability. Embodiments of the invention may therefore be utilized in conjunction with many different types of additional sensors and/or information databases that may provide contextual information useful for determining a patient's cardio-respiratory function and which more accurately accounts for the specific attributes of the patient, activity of the patient, and/or surrounding environment. A database may comprise, for instance, data relating to the individual's medical history or data relating to cardio-respiratory parameter values in different environmental conditions. For example, information or data employed by embodiments may comprise patient activity, vital signs, temperature, etc.

Embodiments may therefore provide a method, device and/or system that provides for user-specific assessment and monitoring of cardio-respiratory function(s) which takes account of contextual factors (including a physical attributes and activity of a patient, for example) in order to provide more accurate assessment and tracking of cardio-respiratory function or parameter. This may enable measurement and tracking of cardio-respiratory for a specific user, whilst enabling the user to partake in desired activities of daily life.

Illustrative embodiments may therefore provide concepts which take account of rules and/or relationships relating to activity and physical attributes of the patient. Dynamic context-based venous information detection and monitoring may therefore be provided by proposed embodiments. In particular, embodiments may communicate information about the venous information in a simple manner (e.g. by visual and/or audible alert) so that a user can readily and easily understand their personal cardio-respiratory function.

As a result, proposed embodiments may be of benefit in any cardio-respiratory function assessment or monitoring applications, especially where users require tailored and/or accurate determination of venous oxygen saturation. One such example may enable patients that are highly susceptible to cardio-respiratory problems to gain a level of independence whilst still managing their potential exposure to cardio-respiratory issues. This may, in turn, improve patient health, hospital efficiency, and available healthcare resources. Embodiments may therefore be of particular benefit for medical applications.

The following description provides a context for the description of elements and functionality of the invention and of how elements of the invention can be implemented.

In the description, the following terms and definitions are used.

A graphical user interface (GUI) is a type of interface that allows users to interact with electronic devices through graphical icons and visual indicators such as secondary notation.

A display device is an electronic display device that can be controlled by a display control device. The display control device can be part of, or operate together with, a processor device.

Generating instructions for displaying a GUI can comprise (or be as simple as) constructing images (Bitmap, JPEG, Tiff or the like) of GUI views to be displayed on a display device using regular methods known in the art. Alternatively, such generation of instructions can comprise more dedicated instructions for real time build-up of a GUI view. The instructions can be in the form of a display control signal.

The invention is at least partly based on the insight that it is advantageous to use a vasculature draining into the internal jugular vein (such as sublingual vasculature/vein of a patient's tongue) for optical monitoring of blood flow or blood volume in response to an airway pressure variation (e.g. temporary change or fluctuation) so as to determine venous information of the patient. In particular, detecting light from the sublingual vein in response to a respiration support device creating a temporary change in positive airway pressure may enable the accurately determination of venous oxygen saturation of the patient. In other words, use of a controllable respiration support device combined with a sublingual optical sensor unit placed at or against a vasculature draining into the internal jugular vein so as to detect light from the vasculature may be used (e.g. processed) to determine a value of cardio-respiratory parameter of the patient.

A concept is suggested which proposes to induce temporary changes in positive airway pressure (e.g. provide pressure stimuli) and monitor variations in blood volume in response to the temporary changes/stimuli using an optical sensor signal which is strongly influenced by the blood volume in the sublingual vein, especially when placed deep (e.g. far from the tip of the tongue or towards the bottom of the tongue).

According to various embodiments, there are proposed several approaches to monitoring cardio-respiratory function of a patient. Turning firstly to FIG. 1, there is depicted an embodiment wherein a sublingual optical sensor unit 10 is positioned at a sublingual vein 15 of the patient's tongue 20.

The optical sensor unit 10 comprises an optical sensor 25 and a light source 30. The light source 30 is adapted to illuminate the underside (e.g. the sublingual vasculature 15) of patient's tongue 20. More specifically, the light source 30 of this embodiment is adapted to emit light of two differing wavelength ranges, namely a first light having a wavelength within a first range of wavelengths and a second light having a wavelength within a second, different range of wavelengths. Here, the first range of wavelength comprises red light (or light having a wavelength towards the red end of the visible light spectrum) and the second range of wavelengths comprises infra-red light. Of course, in other embodiments, the light source may only emit one type (e.g. wavelength range) of light and/or may emit light of wavelengths different to this example of FIG. 1. As another alternative, near-infrared spectroscopy (NIRS) may be used instead of multi-wavelength PPG.

The optical sensor 25 is a photoplethysmography (PPG) sensor and is adapted to detect light from the sublingual vein in response to the illuminating the patient's tongue with light from the light source 30. Thus, in this example the optical sensor unit 10 may be said to operate in a "reflective mode", because the optical sensor 25 and the light source 30 are both situated under the tongue at the sublingual vein 15. Light from the light source 30 therefore illuminates the sublingual vein 15 of the patient's tongue 20 from underneath the tongue 20 and the light reflected by the sublingual vein 15 is then detected by the optical sensor 25. Other examples may, however, employ an optical sensor unit 10 that is said to operate in a "transmissive mode", wherein the optical sensor 25 is situated under the tongue at the sublingual vein 15 and the light source 30 is situated above (e.g. at the upper surface) of the tongue so as to illuminate the tongue from above, or, the opposite situation, wherein the optical sensor 25 is situated on top of the tongue and the light source 30 is situated below the tongue. In such a transmissive mode, the light source 30 illuminates the patient's tongue 20 and the light transmitted through the patient's tongue 20 is then detected by the optical sensor 25.

Based on the detected light, the optical sensor 25 generates a sensor output signal for outputting to a signal processing unit. In this embodiment, the signal processing unit is not integrated into the optical sensor unit 10, but is instead provided as part of a portable computing device (e.g. a smartphone) 100. Of course, in other embodiments, the signal processing unit may be integrated in the optical sensor unit 10.

The embodiment of FIG. 1 further comprises a respiratory support unit 50 adapted to provide a controllable positive airway pressure to an airway of the patient. Here, the respiratory support unit 50 comprises a continuous positive airway pressure, CPAP, ventilator 50 adapted to be positioned (e.g. worn) on the face of the patient so as to cover the mouth and/or nose of the patient. The respiratory support unit 50 is adapted to vary a positive airway pressure applied to an airway of the patient according to control signals provided by a control unit. In this embodiment, the control unit is not integrated into the respiratory support unit 50, but is instead provided as part of the portable computing device (e.g. a smartphone) 100. Of course, in other embodiments, the control unit may be integrated in the respiratory support unit 50.

Using a built-in communication interface, the portable computing device 100 can communicate signals to/from the sublingual sensor unit 10, the respiratory support unit 50 and other, supplementary sensors 110.

Based on control signals from the portable computing device, the respiratory support unit 50 is controlled to a provide a first positive airway pressure to the airway of the patient.

The sublingual sensor unit 10 is then adapted to output a first sensor output signal based on light detected from the tissue in response to provision of the first positive airway pressure. The first sensor output signal is communicated from the sublingual sensor unit 10 to the portable computing device 100.

Further, based on control signals from the portable computing device, the respiratory support unit 50 is controlled to a provide a second, different positive airway pressure to the airway of the patient. The sublingual sensor unit 10 is then adapted to output a second sensor output signal based on light detected from the tissue in response to provision of the second positive airway pressure. The second sensor output signal is communicated from the sublingual sensor unit 10 to the portable computing device 100.

The portable computing device 100 is adapted to process the received first and second sensor output signals in accordance with one or more data processing algorithms to determine a venous information of the patient.

Further, using the conventional communication abilities of the portable computing device 100, the device 100 can communicate with one or more databases so as to obtain information that may be used in determining or monitoring a cardio-respiratory value. Such user-specified information may enable unique traits, circumstances and/or conditions specific to the user or the environment to be accounted for when determining or monitoring venous information. Also, the display of the portable computing device 100 may be used to display a graphical user interface which communicates information about calculated cardio-respiratory functions to a user of the device.

In more detail, the embodiment of FIG. 1 comprises a client device 100, namely a smartphone 100, comprising data acquisition and processing components. The smartphone 100 is adapted to receive sensor output signals from the sublingual optical sensor unit 10 positioned under a patient's tongue (e.g. at the sublingual vasculature) via a wireless communication link. Any suitable short-range or long-range communication links and/or protocols may be employed.

The received sensor output signals from the sublingual optical sensor unit 10 thus comprises data representative of variations in blood volume in response to temporary changes/stimuli in positive airway pressure provided to patient by respiratory support unit 50. This data may be used (e.g. processed in accordance with an algorithm so as to determine a venous information (such as a value of venous oxygen saturation).

For example, the smartphone 100 of this example is adapted to implement a signal processing algorithm which identifies low-frequency variations in optical sensor unit 10 output signal. Here, a respiration rate of the patient is observed as the dominant frequency in the range between 0.08 Hz and 0.5 Hz. The smartphone thus implements a software application which monitors modulation in a low frequency optical sensor unit 10 output signal component which is indicative of the signal response to the deviations in respiration (caused by additional stress in the heart for example). Also, higher frequency variations in the optical sensor unit 10 output signal (for example in the range between 0.6 Hz and 4 Hz) are also used to provide information on average heart rate, heart rate variability, arrhythmias and SpO2, for example. In this way, the smartphone can determine the heart rate and the respiration rate of the patient. The smartphone 100 is also adapted to communicate control signals to the respiratory support unit 50 so as to control the respiratory support unit 50 to provide the second, different positive airway pressure to the airway of the patient based on at least one of: the heart rate; and the respiration rate of the patient.

Furthermore, the smartphone 100 is also adapted to receive information from a supplementary sensor unit 110 which is adapted to sense a value of at least one of: movement; pressure; temperature; and sound. The smartphone 100 is adapted to analyse the determined cardio-respiratory value(s) in combination with the received supplementary sensor 110 output signal(s) to determine at least one of: a refined cardio-respiratory value; an indication of accuracy or reliability; a sleep state of the patient; an activity of the patient; and an indication of event occurrence. In this way, a context of the patient (such as their current activity or physical properties for example) can be taken into account in the process of determining and/or monitoring the cardio-respiratory function of the patient.

The smartphone 100 is also adapted to send and/or receive information to/from a remotely located server 120 via the Internet 125.

The information obtained by the smartphone 100 is processed to assess and identify factors which may influence the determined venous information of the patient. By way of example, environmental information; patient information; and a limit value representative of an acceptable upper limit of a cardio-respiratory value may be used in the determination or monitoring of venous information.

The information/data processing may be done by the smartphone 100, by the 'Cloud', or by any combination thereof. The embodiment of FIG. 1 is therefore implemented as a distributed processing environment in which various types of information/data are processed so as to determine or monitor a cardio-respiratory function of the patient.

The smartphone 100 also comprises an output interface, namely a display 112 and speaker 114 arrangement, adapted to generate an output signal representative of the determined venous information. For example, if a dangerous venous oxygen saturation value is determined or inferred, the user may be advised of the potential threat or danger and guided via voice or visual prompts to mitigate the threat/danger. The smartphone 100 is also adapted to receive (e.g. via its touch sensitive screen 112) a user input signal representative of at least one of: environmental information; patient information; and a limit value representative of an acceptable upper limit of a cardio-respiratory value.

The smartphone 100 therefore provides an interface which enables a user to further specify information or data that may be relevant for the purpose of determining or monitoring a cardio-respiratory value. Such user-specified information enables unique traits, circumstances and/or conditions specific to the user or the environment to be accounted for when determining or monitoring venous information. Put another way, the smartphone 100 enables a user to further specify factors to be included in the determination of venous information, e.g. by specifying a value or value range for a user attribute or activity. This provides many input options, increasing the flexibility and power of risk of cardio-respiratory monitoring.

Additionally, or alternatively, further environmental information and/or patient information may be provided by other sources or services. For example, local weather conditions and/or medical history data from a database of the server 120 can be used.

For example, in an exemplary implementation of the system of FIG. 1, the server 120 comprises a data processor unit and is configured to transmit generated instructions for determining and/or displaying determined venous information to a client device or communication network. In such a configuration, display instructions are made available by the server 120. A user of the smartphone 100 can therefore link with the server 120 to work with the system. In this way, data processing means are remotely located from the portable computing device 100, and a control signal can thus be communicated to the portable computing device 100 via a communication link (e.g. the Internet 125).

Accordingly, a user is provided with an appropriately arranged device that can receive and process information relating to a cardio-respiratory function of a patient. Embodiments may therefore enable a user to monitor venous information over time using a portable computing device, such as a laptop, tablet computer, mobile phone, PDA, etc. The user can obtain an understanding of their cardio-respiratory function, which then enables the user to continue or adapt their planned activities (depending on their tolerance to cardio-respiratory issues for example). Also, a medical professional, technician, researcher, etc. may have an appropriately arranged client device (such as a laptop, tablet computer, mobile phone, PDA, etc.) which is adapted to receive information relating to venous information of a monitored user (e.g. patient). In this way, a user can be provided with guidance at a personal level which takes account of the unique attributes and/or activities of the user, and/or the surrounding environment. This alleviates a need for close monitoring by medical professionals or caregivers, for example. It may also reduce a need for medical intervention or treatment (required as a result of repeated infection for example).

Dedicated data processing means can therefore be implemented at the server 120 for the purpose of determining venous information of a patient, thus relieving or reducing processing requirements at the portable computing device 100.

Thus, it will be understood that processing capabilities may therefore be distributed throughout the system in different ways according to predetermined constraints and/or availability of processing resources of specific embodiments.

Figure 2:
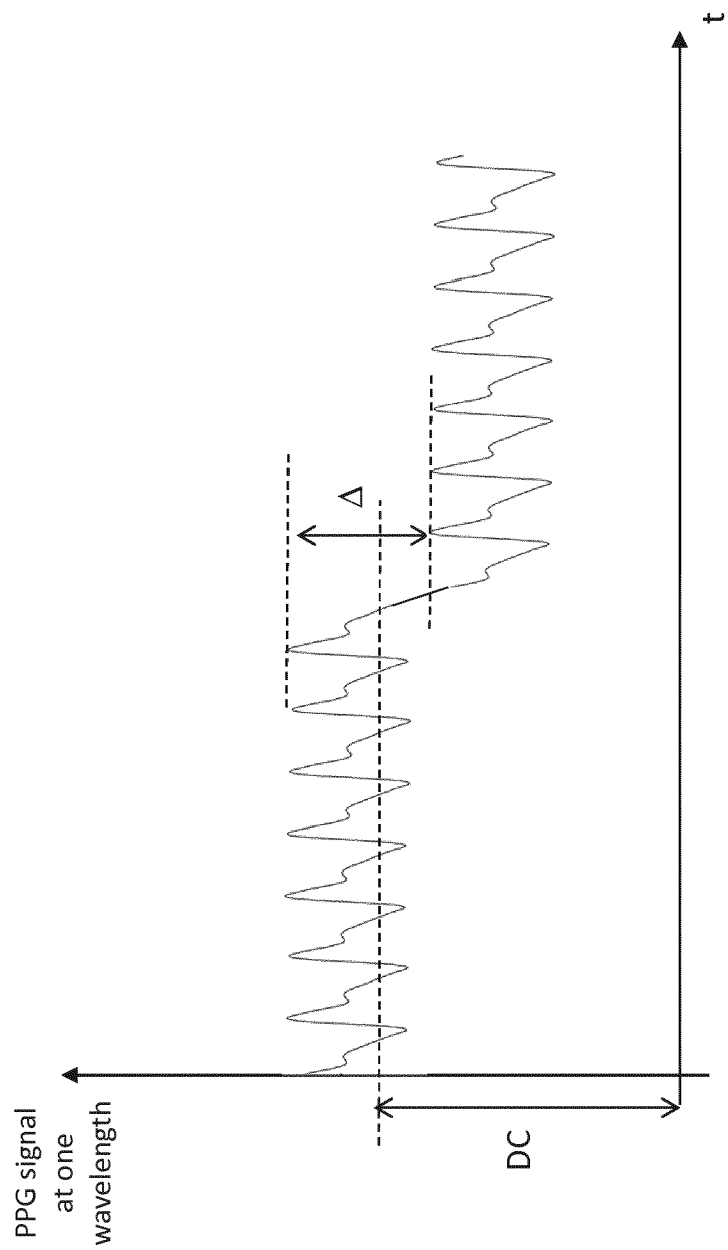
FIG. 2 a depicts PPG signal obtained over time by an exemplary implementation of an embodiment, wherein the monitored time period includes a pressure challenge provided by a mask.

Now, to aid further understanding of the proposed concepts, an exemplary embodiment will be described with reference to FIG. 2. FIG. 2 depicts exemplary variations in a PPG signal (provided by an optical sensor unit according to an embodiment) over time (t), wherein during the illustrated time period a change in positive airway pressure is applied to the patient by a respiratory support unit.

In this embodiment, triggering of the respiratory support unit 50 to modify (e.g. increase) the airway pressure is undertaken at the onset of expiration. This will lead to increased venous pooling, until, after a few heart cycles, the heart is able to output the pooled blood into the pulmonary artery. Therefore, the PPG signals should preferably be measured within a limited number (e.g., three) of heart cycles after triggering the pressure change. After this period, the pressure stimulus can be switched off (e.g. reverted back to a first, steady-state).

Isolation of the venous modulation (A) from the PPG signals can then be performed by subtracting the baseline signal DC. For example, the baseline can be defined as the DC PPG signal before applying the pressure stimulus (i.e., the time-averaged intensity over several heart beats during a single expiration). Alternatively, the DC value can be defined as the time-averaged intensity over the time frame (as shown in FIG. 2), or as the time-averaged intensity after applying the stimulus.

Removal of arterial modulation component may be undertaken by low-pass filtering, or sampling the PPG signals at a specific phase in the heart cycle (e.g. gating) and even the phase in respiratory cycle could be taken into account (e.g. compare the signal before and after the pressure change both during inspiration). The remaining signal is then assumed to represent the venous modulation ($\Delta$) due to the pressure challenge provided by the respiratory support unit, and therefore, be representative of a venous blood sample.

The calculation of the oxygenation can be performed by existing methods, e.g., by the well-known ratio-of-ratios formula: $SvO2 = a \cdot [(\Delta/DC)_{\lambda,1}/(\Delta/DC)_{\lambda,2}] + b$, wherein a and b are calibration constants. By way of example, the calibration constants a and b can be obtained using a calibration table or function.

Figure 3:
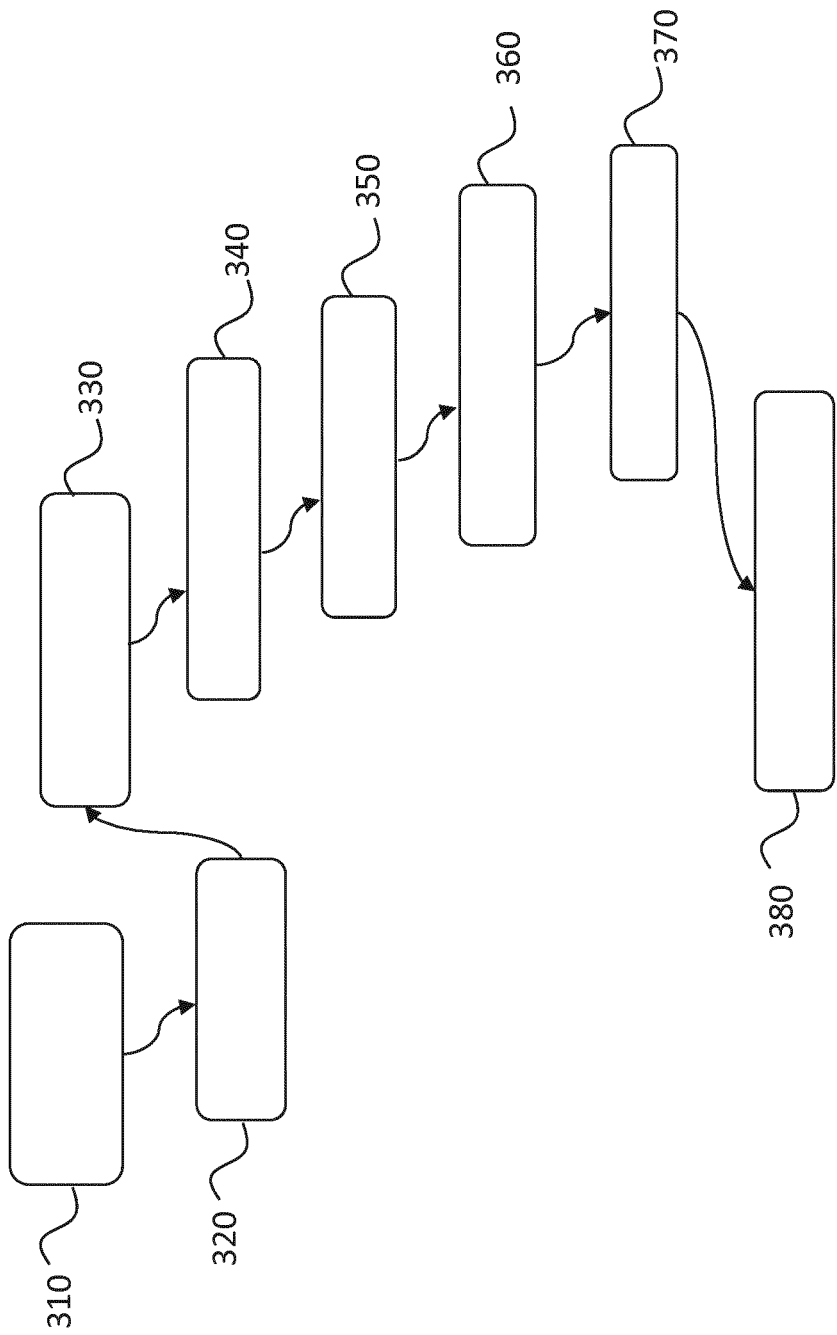
FIG. 3 is a flow diagram of a method according to an embodiment.

Turning now to FIG. 3, there is depicted a flow diagram of a method 300 for monitoring cardio-respiratory function of a patient according to an embodiment.

The method begins with step 310 of appropriately positioning equipment with respect to the patient. In this example, a respiratory support unit (such as a CPAP device) is positioned so as to provide a positive airway pressure to an airway of the patient, and an optical sensor unit is positioned at or adjacent a central-site large vein. For instance, in the example embodiment of FIG. 3, a sublingual optical sensor unit is positioned at a sublingual vasculature of the patient's tongue. Here, the sublingual optical sensor unit is positioned under the patient's tongue towards the rear/back of the tongue and orientated so that the optical sensor of the sublingual optical sensor unit is facing and adjacent the sublingual vein of the tongue. Preferably, the optical sensor unit will be in contact with the underside of the tongue so that it is as close as practically possible to the sublingual vein.

Next, in step 320, the patient's tongue is illuminated with light from one or more light sources. Here, the step of illuminating the patient's tongue comprises positioning a light source against the tongue so that is adapted to shine light at the sublingual vein of the tongue. It also comprises controlling the one or more light sources to emit light having a wavelength within a first range of wavelengths and/or to emit light having a wavelength within a second, different range of wavelengths. More specifically, in this example, the first range of wavelengths comprises visible light and the second range of wavelengths comprises infra-red light. This may of course be different for other embodiments.

In step 320, the respiratory support unit is controlled so as to a provide a first positive airway pressure to an airway of the patient, and light from the sublingual vein is detected by the sublingual optical sensor. The sublingual optical sensor unit then generates a first sensor output signal based on light detected from the tissue in response to provision of the first positive airway pressure. In this way, a sublingual PPG signal is generated in response to the first positive airway pressure.

Typically, the PPG signal is viewed as a low frequency component, considered as DC, and the high frequency component, called AC, contains the blood pulsatility. Thus, the AC component of the PPG can be used to estimate heart rate, heart rate variability, and oxygen saturation (in case multiple wavelengths are used) and may therefore be in the range between 0.5 Hz and 4 Hz. The low frequency components, on the other hand, can be used to extract the features related to respiration and venous pooling.

For example, the heart rate (HR) can be observed as a dominant frequency in the range of 0.5 Hz and 3 Hz. For example, respiration rate (RR) can be observed as the dominant frequency in the range between e.g. 0.08 and 0.4 Hz, and respiration rate variability (RRV) is based on the changes in the RR over time. Accordingly, changes in the depth of respiration can be interpreted from amplitude variations of the PPG signal at the respiration frequency.

Nevertheless, in some embodiments, the AC signal component could also be part of the sensor output signal and processed to obtain information regarding average heart rate, heart rate variability, arrhythmias and SpO2.

Accordingly, based on the sublingual PPG signal, values of the patient's heart rate and respiration are derived in step 330. Based on such derived cardio-respiratory values of the patient's, control signals for the respiratory support unit and sublingual optical sensor are generated in step 340. By way of example, the control signals comprise a trigger signal for controlling the respiratory support unit to modify the positive airway pressure and a time window within which the sublingual optical sensor is to obtain a PPG signal in response to provision of the modified positive airway pressure. An example may be to trigger at the foot of the first heartbeat every tenth breath of the patient and an example of the time window may be the time period of three heartbeats after the provision of the modified pressure.

Based on the generate control signals, the respiratory support unit is controlled (in step 350) to provide a second, different positive airway pressure to the airway of the patient, and the optical sensor unit is controlled (in step 360) to obtain (at a specified time period after the pressure change) a second PPG signal based on light detected from the tissue in response to provision of the modified positive airway pressure.

In step 370, the venous modulations are isolated from the second PPG signal. For example, the delta/change in the DC signal is determined for the first few heartbeats following the provision of the modified positive airway pressure.

Finally, in step 380, venous information of the patient is determined based on the obtained PPG signals. In particular, step 380 of FIG. 3 comprises calculating venous oxygen saturation using a formula that describes SvO2 as being a function of $(\Delta/DC)_{\lambda,1}/(\Delta/DC)_{\lambda,2}$, such as $SvO2 = a \cdot [(\Delta/DC)_{\lambda,1}/$ $(\Delta/DC)_{\lambda 2}]+b$, wherein a and b are calibration constants. As has been mentioned above, the calibration constants a and b can be obtained using a calibration table or function.

From the above description of the flow diagram in FIG. 3, it will be understood that embodiments may provide a concept for monitoring venous information of a patient. The proposed concept may comprise positioning an optical sensor at (e.g. adjacent, next to, neighbouring) a central-site large vein of a patient. Light transmitted through the vein may then be detected by the optical sensor and the detected light may be used (e.g. processed according to one or more algorithms) to determine a value of a cardio-respiratory functions of the patient. In particular, variations in the detected light in response to temporary airway pressure changes provided by a respiratory support unit may be used to determine venous information such as venous oxygen saturation.

Although the use of a CPAP device to provide temporary or pulsed pressure changes has been described above, other pressure challenges may be provided (e.g. only during expiration or inspiration) or forced oscillation techniques may be employed. Also, alternative triggering concepts may be employed (e.g. based on electrocardiogram signals) and alternative respiration measures may be used.

Determining venous information may also comprise taking account of historical information relating to previously determined venous information of the patient. Further, additional sensors may be employed to detect one or more supplementary values of other physical attributes or parameters of the patient. Such supplementary values may be used in combination with the detected PPG signals and/or determined venous information to infer or determine other information (such as an indication of accuracy or reliability, a sleep state of the patient, an activity of the patient, or an indication of event occurrence for example) and/or confirm/validate the determined venous information.

For such purposes, proposed concepts may employ (or be employed on) at least one processor.

Thus, there may be provided a computer program product downloadable from a communications network and/or stored on a computer readable medium and/or microprocessor-executable medium wherein the computer program product comprises computer program code instructions, which when executed by at least one processor, implement a method according to a proposed embodiment.

Figure 4:
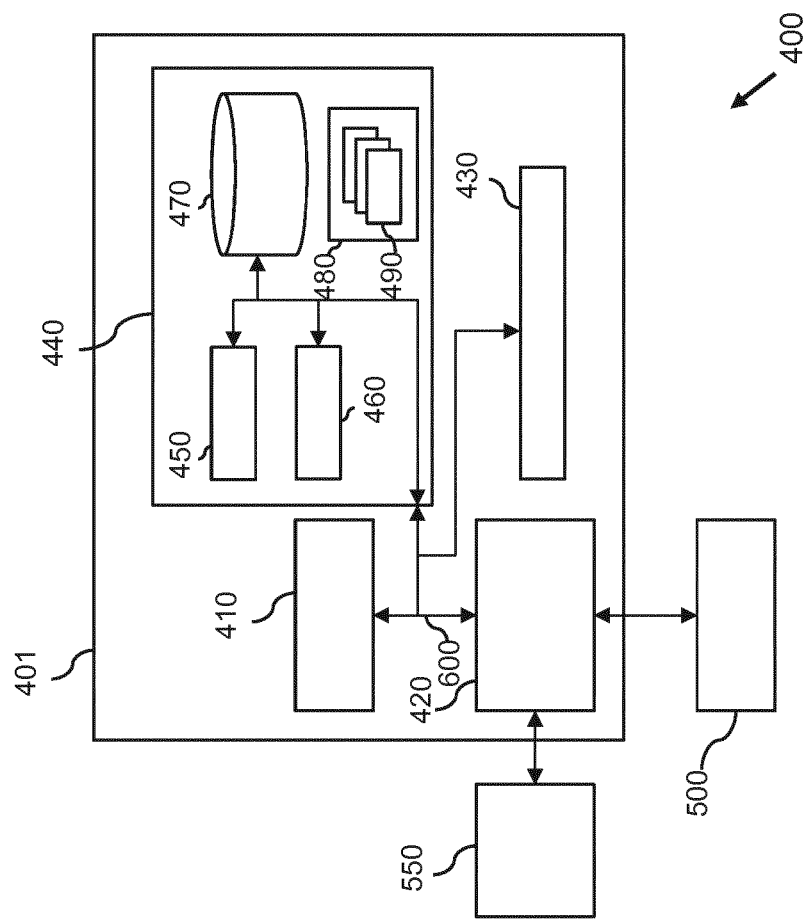
FIG. 4 illustrates an example of a computer system within which one or more parts of an embodiment may be employed.

By way of example, as illustrated in FIG. 4, embodiments may comprise a computer system 401, which may form part of a networked system 400. The components of computer system/server 401 may include, but are not limited to, one or more processing arrangements, for example comprising processors or processing units 410, a system memory 440, and a bus 600 that couples various system components including system memory 440 to processing unit 410.

Bus 600 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 401 typically includes a variety of computer system readable media. Such media may be any available media that is accessible by computer system/server 401, and it includes both volatile and non-volatile media, removable and non-removable media.

System memory 440 can include computer system readable media in the form of volatile memory, such as random access memory (RAM) 450 and/or cache memory 460. Computer system/server 401 may further include other removable/non-removable, volatile/non-volatile computer system storage media. By way of example only, storage system 440 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 600 by one or more data media interfaces. As will be further depicted and described below, memory 440 may include at least one program product having a set (e.g., at least one) of program modules that are configured to carry out the functions of embodiments of the invention.

Program/utility 480, having a set (at least one) of program modules 490, may be stored in memory 440 by way of example, and not limitation, as well as an operating system, one or more application programs, other program modules, and program data. Each of the operating system, one or more application programs, other program modules, and program data or some combination thereof, may include an implementation of a networking environment. Program modules 490 generally carry out the functions and/or methodologies of embodiments of the invention as described herein.

Computer system/server 401 may also communicate with one or more external devices 500 such as a keyboard, a pointing device, a display 550, etc.; one or more devices that enable a user to interact with computer system/server 401; and/or any devices (e.g., network card, modem, etc.) that enable computer system/server 401 to communicate with one or more other computing devices. Such communication can occur via Input/Output (I/O) interfaces 420. Still yet, computer system/server 401 can communicate with one or more networks such as a local area network (LAN), a general wide area network (WAN), and/or a public network (e.g., the Internet) via network adapter 430. As depicted, network adapter 430 communicates with the other components of computer system/server 401 via bus 600. It should be understood that although not shown, other hardware and/or software components could be used in conjunction with computer system/server 401. Examples, include, but are not limited to: microcode, device drivers, redundant processing units, external disk drive arrays, RAID systems, tape drives, and data archival storage systems, etc.

Thus, there is proposed a concept for providing guidance regarding cardio-respiratory function at a personal level which employs optical sensing of a central-site vein in response to temporary airway pressure changes. By sensing variations in blood volume in the central site vein in response to temporary airway pressure changes, venous information of the person may be obtained.

At this point, it is noted that the above described embodiments are merely example embodiments and that several extensions thereto and/or variations may be made.

For example, several types of supplementary monitoring/sensing devices can be envisaged, including clip-on devices, smart textiles, mouth inserts, etc.

Data from the system may be combined with personal data on health and well-being to generate a personal profile of "safe" and "risky" activities, locations and interactions. Data may also be transmitted for the benefit of other peer users or patients interested in cardio-respiratory functions, and such data could serve as input to complication avoidance software.

Other suitable extensions and variations to the above disclosed embodiments will be apparent to the skilled person.

For example, embodiments may be adapted to implement flexible thresholds that can be adapted according to user and/or with respect to time. In this way, it may be possible to have more or less strict versions of algorithms used to create alerts or notifications.

Also, also mentioned above, the optical sensor may comprise several light sources (e.g. LEDs) and/or several photo detectors. They may be arranged in an array-like structure. The optical sensor could also comprise a CCD chip or use laser-speckle technique.

In another embodiment, the optical sensor may be a (remote) camera, for example a camera that a GP has in his hand. The patient may be asked to lift his/her tongue up (or have his/her tongue lifted up by an additional device) in order to make the area around the sublingual vein visible to the camera.

A preferred implementation may be to only inform a user when a cardio-respiratory issue or anomaly is detected. This may help to ensure a seamless solution without inhibiting social interaction.

The proposed concept has the advantage that a network of portable computing device with monitoring and/or communication functions can be easily transformed into a cardio-respiratory function monitoring system.

Aspects of the present invention may be embodied as a cardio-respiratory function monitoring method or system at least partially embodied by a portable computing device or distributed over separate entities including a portable computing device. Aspects of the present invention may take the form of a computer program product embodied in one or more computer-readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Such a system, apparatus or device may be accessible over any suitable network connection; for instance, the system, apparatus or device may be accessible over a network for retrieval of the computer readable program code over the network. Such a network may for instance be the Internet, a mobile communications network or the like. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fibre, a portable compact disc read-only memory (CD-ROM), an optical storage device, a magnetic storage device, or any suitable combination of the foregoing. In the context of the present application, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fibre cable, RF, etc., or any suitable combination of the foregoing.

Computer program code for carrying out the methods of the present invention by execution on the processor 110 may be written in any combination of one or more programming languages, including an object oriented programming language such as Java, Smalltalk, C++ or the like and conventional procedural programming languages, such as the "C" programming language or similar programming languages. The program code may execute entirely on the processor 110 as a stand-alone software package, e.g. an app, or may be executed partly on the processor 110 and partly on a remote server. In the latter scenario, the remote server may be connected to the head-mountable computing device 100 through any type of network, including a local area network (LAN) or a wide area network (WAN), or the connection may be made to an external computer, e.g. through the Internet using an Internet Service Provider.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions to be executed in whole or in part on the data processor 110 of the cardiopulmonary resuscitation coordination system including portable computing device, such that the instructions create means for implementing the functions/acts specified in the flowchart and/or block diagram block or blocks. These computer program instructions may also be stored in a computer-readable medium that can direct the cardiopulmonary resuscitation guidance system including the portable computing device to function in a particular manner.

The computer program instructions may, for example, be loaded onto the portable computing device 100 to cause a series of operational steps to be performed on the portable computing device 100 and/or the server 120, to produce a computer-implemented process such that the instructions which execute on the portable computing device 100 and/or the server 120 provide processes for implementing the functions/acts specified in the flowchart and/or block diagram block or blocks. The computer program product may form part of a patient monitoring system including a portable computing device.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. Apparatus for monitoring cardio-respiratory function of a patient, the apparatus comprising:
    sublingual optical sensor unit adapted to be positioned at sublingual vasculature of the patient's tongue, to detect light from sublingual vasculature of the patient and to generate sensor output signals based on the detected light;
    a respiratory support unit adapted to provide a controllable positive airway pressure to an airway of the patient;
    a control unit adapted to control the respiratory support unit to a provide a first positive airway pressure to the airway of the patient and to receive a first sensor output signal from the optical sensor unit, the first sensor output signal being based on light detected from the tissue in response to provision of the first positive airway pressure, and further adapted to control the respiratory support unit to provide a second, different positive airway pressure to the airway of the patient and to receive a second output signal from the optical sensor unit, the second sensor output signal being based on light detected from the tissue in response to provision of the second positive airway pressure; and
    a processing unit adapted to determine venous information of the patient based on how the first and second sensor output signals vary from provision of the first positive airway pressure to provision of the second positive airway pressure.

2. The apparatus of claim 1, wherein the control unit is adapted to control the respiratory support unit to provide a pulsed application of the second, different positive airway pressure to the airway of the patient.

3. The apparatus of claim 1, wherein the processing unit is adapted to determine at least one of: the heart rate; and the respiration rate of the patient based on at least one of: a sensor output signal from the optical sensor; and positive airway pressure provided by the respiratory support unit to the airway of the patient.

4. The apparatus of claim 3, wherein the control unit is adapted to control the respiratory support unit to provide the second, different positive airway pressure to the airway of the patient based on at least one of: the heart rate; and the respiration rate of the patient.

5. The apparatus of claim 3, wherein the timing of the first and second sensors output signals is based on the phase in at least one of: the cardiac cycle; and the respiratory cycle.

6. The apparatus of claim 1, wherein the venous information comprises a value of venous oxygen saturation.

7. The apparatus of claim 1, where the control unit is further adapted to control the respiratory support unit based on the determined venous information.

8. The apparatus of claim 1, wherein the optical sensor unit comprises at least one of: a photoplethysmography sensor; a laser speckle sensor; a laser Doppler sensor; and a camera.

9. The apparatus of claim 1, further comprising one or more light sources adapted to emit light having a wavelength within a first range of wavelengths and to emit light having a wavelength within a second, different range of wavelengths, and preferably wherein the first range of wavelength comprises visible light and the second range of wavelengths comprises infra-red light.

10. The apparatus of claim 1, wherein the respiratory support unit comprises a continuous positive airway pressure, CPAP, ventilator.

11. A method for monitoring cardio-respiratory function of a patient, the method comprising:
    controlling a respiratory support unit to a provide a first positive airway pressure to an airway of the patient;
    obtaining, from sublingual optical sensor unit positioned at sublingual vasculature of the patient's tongue, a first sensor output signal based on light detected from the sublingual vasculature in response to provision of the first positive airway pressure,
    controlling the respiratory support unit to provide a second, different positive airway pressure to the airway of the patient
    obtaining from the sublingual optical sensor unit positioned at sublingual vasculature of the patient's tongue, a second sensor output signal based on light detected from the sublingual vasculature in response to provision of the second positive airway pressure; and
    determining venous information of the patient based on how the first and second sensor output signals from provision of the first positive airway pressure to provision of the second positive airway pressure.

12. The method of claim 11, wherein the step of controlling the respiratory support unit to provide the second, different positive airway pressure to the airway of the patient is based on at least one of: the heart rate; and the respiration rate of the patient, and further comprising providing a control signal to the respiratory support unit by the control unit that is gated by the phase in at least one of: the cardiac cycle; and the phase in the respiratory cycle.

13. A computer program product downloadable from a communications network and stored on a non-transitory computer readable medium and/or non-transitory microprocessor-executable medium wherein the computer program product comprises computer program code instructions, which when executed by at least one processor, implement a method as claimed in claim 11.

* * * * *